(12) United States Patent
Okuda et al.

(10) Patent No.: US 6,706,030 B1
(45) Date of Patent: Mar. 16, 2004

(54) ABSORBENT ARTICLE

(75) Inventors: Yasuyuki Okuda, Tochigi (JP);
Hisanori Watanabe, Tochigi (JP);
Hidekazu Ito, Tochigi (JP); Takao Koyama, Tochigi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/856,646

(22) PCT Filed: Mar. 7, 2000

(86) PCT No.: PCT/JP00/01368
§ 371 (c)(1),
(2), (4) Date: May 24, 2001

(87) PCT Pub. No.: WO00/53140
PCT Pub. Date: Sep. 14, 2000

(30) Foreign Application Priority Data

Mar. 10, 1999 (JP) .............................................. 11-63345
Dec. 8, 1999 (JP) ............................................ 11-348995

(51) Int. Cl.[7] .......................... A61F 13/15; A61F 13/20
(52) U.S. Cl. ........................... 604/385.29; 604/385.24; 604/385.27; 604/385.28
(58) Field of Search .......... 604/385.19, 385.21–385.31, 604/393–396

(56) References Cited

U.S. PATENT DOCUMENTS

| | | | | |
|---|---|---|---|---|
| 4,300,562 A | * | 11/1981 | Pieniak | 604/385.26 |
| 4,704,116 A | * | 11/1987 | Enloe | 604/385.27 |
| 4,795,454 A | * | 1/1989 | Dragoo | 604/385.27 |
| 5,021,051 A | * | 6/1991 | Hiuke | 604/385.27 |
| 5,026,364 A | * | 6/1991 | Robertson | 604/385.3 |
| 5,196,000 A | * | 3/1993 | Clear et al. | 604/385.29 |
| 5,527,302 A | * | 6/1996 | Endres et al. | 604/385.21 |
| 5,569,234 A | * | 10/1996 | Buell et al. | 604/385.29 |
| 5,582,606 A | * | 12/1996 | Bruemmer et al. | 604/385.28 |
| 5,643,243 A | | 7/1997 | Klemp | |
| 5,645,543 A | * | 7/1997 | Nomura et al. | 604/385.27 |
| 5,769,838 A | | 6/1998 | Buell et al. | |
| 6,123,694 A | * | 9/2000 | Pieniak et al. | 604/385.28 |
| 6,497,694 B1 | * | 12/2002 | Rosch et al. | 604/385.28 |

FOREIGN PATENT DOCUMENTS

| | | |
|---|---|---|
| EP | 321732 | 6/1989 |
| EP | 648482 | 4/1995 |
| EP | 925768 | 6/1999 |
| EP | 945111 | 9/1999 |
| GB | 2 250 921 A | 6/1992 |
| TW | 312133 | 8/1997 |
| WO | 9720532 | 6/1997 |

* cited by examiner

Primary Examiner—Karin Reichle
(74) Attorney, Agent, or Firm—Birch, Stewart, Kolasch & Birch, LLP (57) ABSTRACT

An absorbent article includes a liquid-permeable topsheet, a liquid-impermeable antileakage sheet, a liquid-retentive absorbent core, having a substantially elongate shape, and having upstanding guards formed on longitudinal left and right opposing side portions of the absorbent article, the upstanding guards are provided with a plurality of upstanding guard elastic members so as to form a gather over the entire region in the widthwise direction of the upstanding guard, the upstanding guard is sectioned into a free end region, a central region and a basal end region so as to trisect it in its widthwise direction, and the stress of the free end region is larger than that of the other regions.

19 Claims, 7 Drawing Sheets

ABSORBENT ARTICLE

This application is the national phase under 35 U.S.C. §371 of PCT International Application No. PCT/JP00/01368 which has an International filing date of Mar. 7, 2000, which designated the United States of America and was published in English.

TECHNICAL FIELD

The present invention relates to an absorbent article which exhibits excellent anitleakage properties and also gives excellent feel during use.

BACKGROUND ART

Various kinds of absorbent articles have been proposed in the conventional art. These articles include disposable diapers having a substantially elongate shape. The diaper's components can include a liquid-permeable topsheet, a liquid-impermeable antileakage sheet, a liquid-retentive absorbent core, and an upstanding guard formed on longitudinal left and right opposing side portions of the diaper.

The conventional upstanding guard has a strip of elastic disposed on the distal end side, and the strip of elastic rises upwardly of the diaper. However, this structure fails to keep the guard sufficiently erect during use. Thus, the guard fails to give the desired leakage prevention effect.

U.S. Pat. No. 5,643,243 has proposed to arrange a plurality of elastic members on the upstanding guard, but the conventional upstanding guards have a plurality of elastic members that are not closely fitted to the wearer's skin, thus failing to attain sufficient leakage prevention properties.

SUMMARY OF THE INVENTION

It is, therefore, an object of the present invention to provide an absorbent article such as a disposable diaper in which an upstanding guard exhibits a good fit to the wearer's skin, and the leakage prevention properties are improved.

The present invention has achieved the above object by providing an absorbent article including a liquid-permeable topsheet, a liquid-impermeable antileakage sheet and a liquid-retentive absorbent core, having a substantially elongate shape, and being provided with upstanding guards on the longitudinal left and right opposing side portions of the absorbent article, wherein the upstanding guards are provided with a plurality of upstanding guard elastic members so as to form a gather over the entire region in the widthwise direction of the upstanding guard, and wherein the upstanding guard is sectioned into a free end region, a central region and a basal end region so as to trisect it in the widthwise direction, the stress of the free end region being larger than that of the other regions.

The invention, in part, pertains to the central region having smaller stress than that of the free end region and the basal region. Also, the stress of the free end region can be from 10 cN to 100 cN, the stress of the basal end region can be from 5 cN to 90 cN and the stress of the central region is from 5 cN to 80 cN.

BRIEF DESCRIPTION OF THE DRAWINGS

The present invention will now be described with reference to the following drawings, wherein.

DETAILED DESCRIPTION OF THE INVENTION

Figure 1:
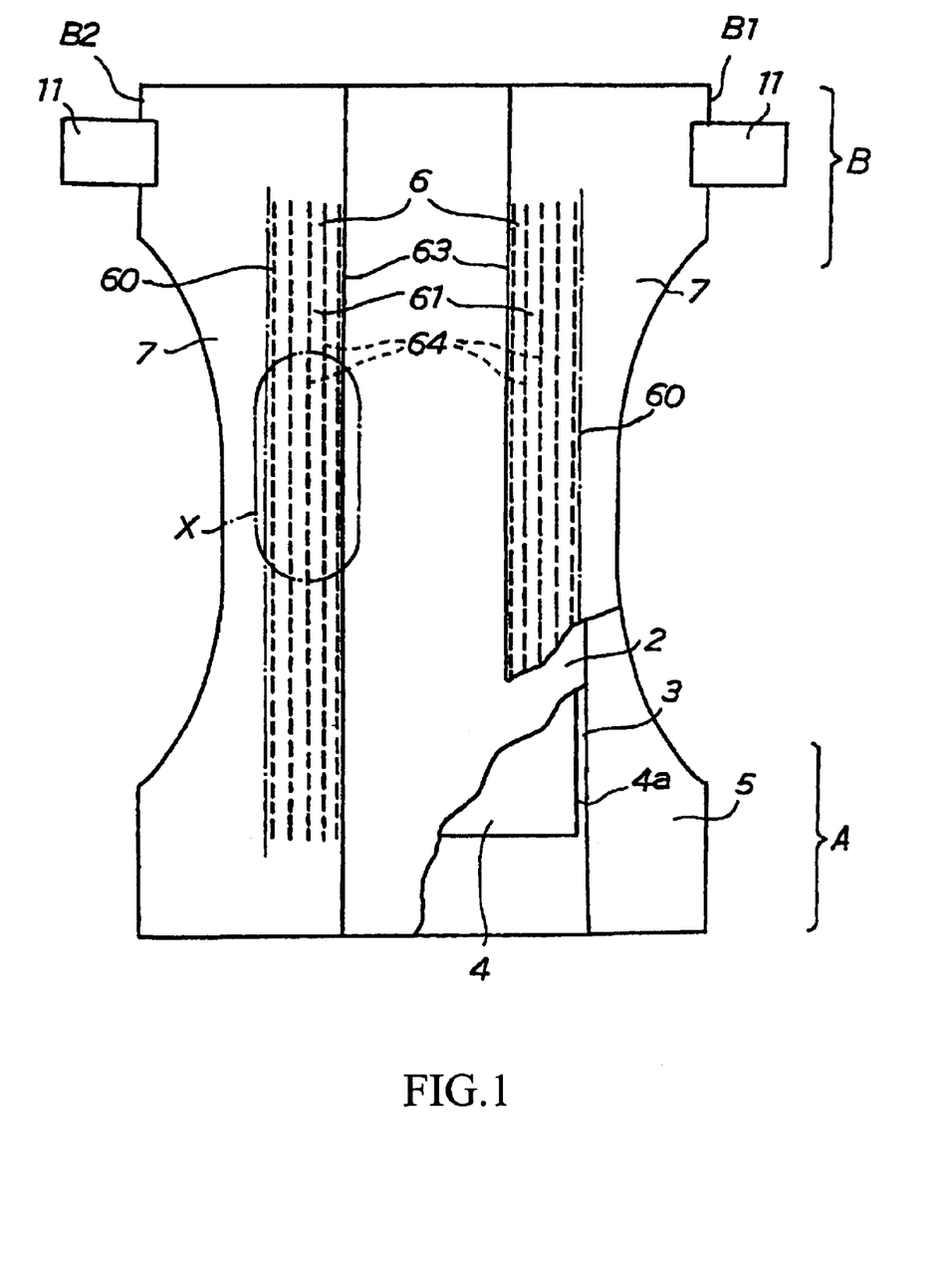
FIG. 1 is a plan view partly in section showing a disposable diaper according to an embodiment of the invention.
Figure 2:
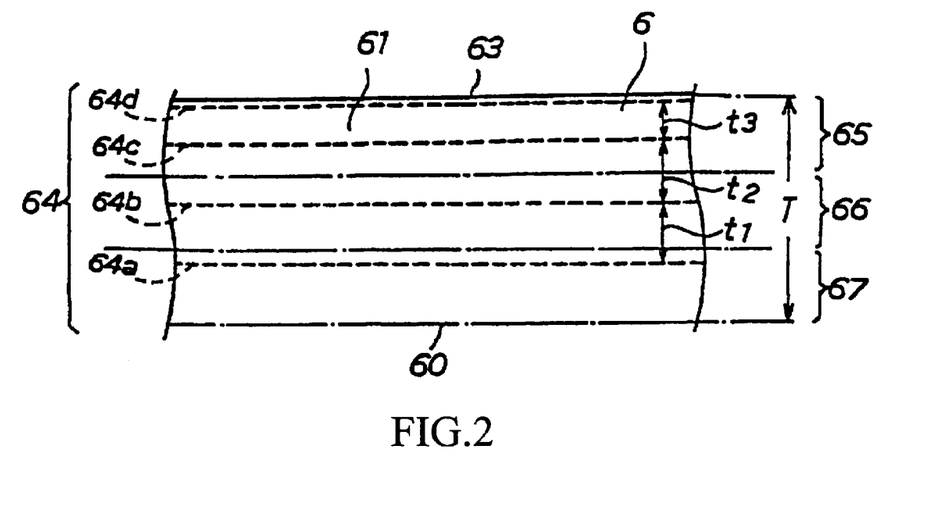
FIG. 2 is an enlarged plan view of the X portion shown in FIG. 1.

A disposable diaper of the first embodiment of the present invention, will now be described. The disposable diaper 1 as the absorbent article according to the present invention, as shown in FIGS. 1 and 2, includes a liquid-permeable topsheet 2, a liquid-impermeable antileakage sheet 3, and a liquid-retentive absorbent core 4, having a substantially elongate shape, and being provided with upstanding guards 6 provided on the longitudinal left and right opposing side portions of the diaper.

The disposable diaper 1 of this embodiment is arranged in such a manner that the topsheet 2 and the antileakage sheet 3 sandwich and fix the absorbent core 4. Left and right opposing side portions B1, B2 of the back side portion B are each provided with a fastening tape 11.

The top surface of the antileakage sheet 3 is provided with an outer layer nonwoven fabric 5. The outer layer nonwoven fabric 5 extends such that the opposing side edges thereof locate outwardly of the side edges 4a of the absorbent core 4. The extended portion of the outer layer nonwoven fabric 5 is sealed to a sheet material 61 for forming the upstanding guard to thereby form a pair of left and right side flap portions 7. The sheet material 61 adheres to the topsheet 2 in the upper position of the absorbent core 4 to thereby form a basal end 60.

The disposable diaper 1 of this embodiment is provided with four upstanding guard elastic members 64 (64a, 64b, 64c, 64d) in the upstanding guard 6 so that a gather is formed in the upstanding guard 6 over the entire region in the widthwise direction thereof. When the upstanding guard 6 is sectioned into a free end region 65, a central region 66 and a basal end region 67 so as to trisect it in the widthwise direction, the stress of the free end region 65 is larger than that of the other regions 66 and 67.

If the stress of the central region 66 is larger than that of the free end region 65, the central region 66 has a reduced function as a buffer region for buffering outer factors, thus failing to ensure the stability of the free end region 65 during wear.

If the stress of the basal end region 67 is larger than the free end region 65, the basal end region 67, which should be a support region, also has an effect as a fit region and is likely to move to the groin, failing to maintain the upstanding guard in a stable shape.

In more detail, in this embodiment, the upstanding guard elastic members 64a, 64b, 64c, 64d each are in a string form and are disposed linearly along the longitudinal direction of the disposal diaper 1 and in parallel with each other.

As shown in FIG. 2, elastic members 64a, 64b, 64c, 64d are arranged so as to have an unequal interval between the adjacent members. The free end region 65 has two elastic members of the third and fourth elastic members 64c, 64d, the central region 66 has one elastic member of the second elastic member 64b, and the basal end region 67 has one elastic member of the first elastic member 64a.

The first, second, third and fourth elastic members of 64a, 64b, 64c, 64d in this embodiment are made of the same members at the same stretching ratio, so that each elastic member has the same stress. Thus, the central region 66 and the basal end region 67 each provided with only one elastic member has smaller stress than the free end region 65 provided with two elastic members, which constitution imparts the highly fit properties and antileakage properties to the diaper.

Specifically, the elastic members 64a, 64b, 64c, 64d each preferably have a stress of 5 to 50 cN from the viewpoint of close fit to the wearer.

The stress of the free end region 65 is preferably 10 to 100 cN, more preferably 10 to 80 cN, from the viewpoint of exhibiting a high level of fit and antileakage properties while exhibiting a soft touch to the skin.

The stress of the central region 66 is preferably 5 to 80 cN, more preferably 5 to 60 cN, from the viewpoint of ensuring the stability of the free end region (fit region) during use by allowing the central region to function as a buffer region for buffering the deformation of the diaper body or forces caused by movements of the wearer.

The stress of the basal end region 67 is preferably 5 to 90 cN, more preferably 5 to 70 cN, from the viewpoint of exhibiting a high degree of fit properties and preventing an excessively strong touch to the skin by allowing the basal end region 67 to reliably receive forces by movements of the wearer.

The difference between the stress of the free end region 65 and the basal end region 67 or the central region 66 in a 50% stretched condition is preferably 5 cN or more, more preferably 10 cN or more, most preferably 10 to 50 cN, from the viewpoint of exhibiting the advantageous effects of each region, a high degree of fit properties to the skin and good standing properties of the upstanding guard.

The stress of each elastic member and the stress of each region in the present invention can be measured in the following manner.

Stress of the Elastic Member; If the elastic member which has not been applied to an upstanding guard is available, the following measuring method is applicable thereto as it is. If it has been applied to an upstanding guard, the elastic member is removed from the upstanding guard and subjected to the following measuring method. If the the elastic member is fixed by an adhesive or the like, the separation is preferably done by subjecting it to heat with a drier or the like to the extent that the physical property is not modified.
<Measuring Method>

A sample of an elastic member was subjected to a tensile test under the conditions of 100 mm in preliminary chuck distance and 300 mn/min in crosshead moving rate using a Tensilon tensile tester (manufactured by Orientic Corp.) to stretch the sample up to 100% and measure S—S curve line. The weight at a point of 50% stretching was measured as the stress of the elastic member.

Stress of Region: An upstanding guard of each region having a length dimension of 140 mm was cut out. The upstanding guard means the portion between the basal end to the free end. Each region can be cut out by trisecting the region from the basal end to the free end. The measuring method applied to the elastic member was repeated to measure the weight at a point of 50% stretching with respect to each region as the stress of the region. If the fixed elastic member is not in a 100% stretched condition, then the elastic member should be stretched so as to reach its maximum stretching elongation, followed by measuring of its S-S curve line. The weight at a point of 50% stretching was measured as the stress.

The following measures are taken in the case that the region cannot be measured independently because of the presence of an elastic member in the boundary portion of each region or for another reason.
1. In the case that the width of the elastic member is smaller than one third of the width of each region:
   a) If an elastic member exists on the boundary line between the free end region and the central region, it is treated as the elastic member of the free end region.
   b) If an elastic member exists on the boundary line between the central region and the basal end region, it is treated as the elastic member of the basal end region.
2. In the case that the width of the elastic member is larger than one third of the width of each region, including the case that a string elastic member curves across each region and the width of the portion provided with the string elastic member is larger than one third of the width of the region:

After measuring the stress of each region excluding the elastic member of the boundary portion and the stress of the elastic member in the boundary portion, the latter stress thus measured is added to the former stress in a proportion of the existing ratio of the elastic member occupied in each region to thereby obtain the stress of each region.

For example, if the stress of the free end region excluding the elastic member of the boundary portion is 30 cN and that of the central region excluding the elastic member of the boundary portion is 10 cN, the stress of the elastic member of the boundary portion is 20 cN, the existing ratio of the elastic member at the free end region is 0.7 and that in the central region is 0.3, then the stress of the free end region is 30+20×0.7=44 cN, and the stress of the central region is 10+20×0.3=16 cN.

The existing ratio can be determined from the area ratio of the elastic member in the region. If the elastic member is disposed generally parallel with the region boundary portion, the ratio of the width occupied in each region is the existing ratio. The "width of the elastic member" referred to here is the width when the elastic member in the predetermined position of the upstanding guard is at maximal expansion, i.e., in an expanded manner as shown in FIG. 1. The same should be applied to the existing ratio.

Among four upstanding guard elastic members 64a, 64b, 64c, 64d, the interval between the upstanding guard elastic member 64a (referred to as the "first elastic member" hereinafter) arranged in the most basal end 60 side and the upstanding guard elastic member 64b (referred to as the "second elastic member" hereinafter) arranged second from the basal end 60 is defined as t1 (referred to as the "first interval" hereinafter). The interval between the upstanding guard elastic member 64c (referred to as the "third elastic member" hereinafter) arranged second from the free edge end 63 and the second elastic member 64b is defined as t2 (referred to as the "second interval" hereinafter). The interval between the upstanding guard elastic member 64d (referred to as the "fourth elastic member" hereinafter) arranged in the free edge end 63 and the third elastic member 64c is defined as t3 (referred to as the "third interval" hereinafter). As shown in FIG. 2, the distance between the basal end 60 to the free edge end 63 of the upstanding guard 64 is defined as "T" (referred to as "upstanding guard width" hereinafter). The relationship of the upstanding guard width T, the first interval t1, the second interval t2 and the third interval t3 is preferably t1+t2+t3≦T, and the relationship is preferably t3≦T/3, more preferably t1≦t2, most preferably, t3<t1<t2 from the viewpoint of exhibiting the aforesaid desired effects.

The upstanding guard width T is a matter of design choice depending on the type of the absorbent article, but it is preferably 15 to 55 mm from the viewpoint of holding efficiency of the waste materials and the shape of the upstanding guard when it is worn.

In addition, the stress of each elastic member may be made non-uniform to obtain a desired advantageous effect.

For example, the stress of the elastic members 64c, 64d existing in the free end region 65 may be different from the stress of the elastic member of the other regions. According to the stress of an elastic member a little weaker than that of other regions' elastic member, soft feeling to the skin is obtainable and traces of the elastic member on the skin is preventable.

In addition, the stress of the central region 66 may be made smaller than that of the other region by adjusting the stress of the elastic member or another adjustment. This modification is preferable because the central region buffers the force or the like caused by the free end region and the stability of the free end region during wear can be ensured. However, if no elastic member is provided so as to extremely weaken the stress or an elastic member having extremely weak stress is provided, the central region collapses when receiving the outer force, failing to exhibit the buffering ability. Thus, the stress of the central region is preferably within the above-identified range as well as smaller than the other regions.

The disposable diaper of this embodiment can be made of any component members conventionally used in the art of disposable diapers, without any particular limitation, but it is preferred that the upstanding guard elastic members is composed of thread rubber made of known elastic materials.

The disposable diaper of this embodiment can be used in the same manner as a conventional flat-type disposable diaper.

In the disposable diaper 1 of the present invention, the free end region 65 having a larger stress tends to move to the narrowest part of the crotch of the wearer. The standing property of the upstanding guard 6 improves, and the fit of the guard to the crotch is ensured to thereby prevent waste materials from leaking caused by crossing over the upstanding guard 6. Besides, sufficient antileakage property can be obtained without rendering the stress of each elastic member unnecessarily high, so that the pressure of contracting force of the elastic member to the skin can be reduced, and diaper rash and skin sores can be prevented. That is, even if the stress of the whole upstanding guard is not so large, the standing property of the upstanding guard can be sufficiently retentive, so that the diaper fits the wearer comfortably without hurting the skin.

The disposable diaper of this embodiment can be produced by any methods as used in the production of conventional flat-type disposable diapers without any particular limitation.

Next, the second embodiment of the present invention will be explained.

Particularly, the points different from the first embodiment will be explained in detail hereinafter. Omission of explanation means that the points are the same as the first embodiment.

Figure 3:
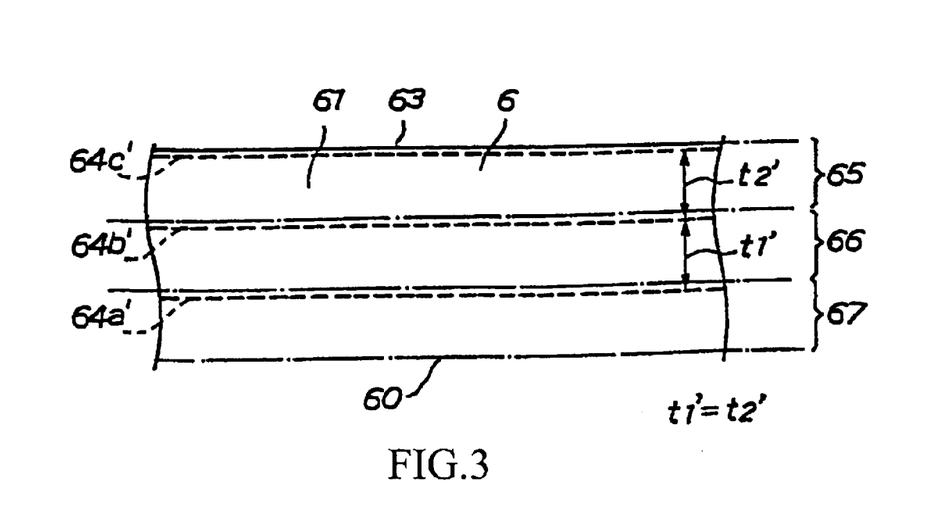
FIG. 3 is a partially enlarged plan view showing a disposable diaper as a second embodiment of the absorbent article of the present invention corresponding to FIG. 2.

The disposable diaper 1 as the absorbent article of this embodiment, is the same as 15 the first embodiment, including a liquid-permeable topsheet 2, a liquid-impermeable antileakage sheet 3 and a liquid-retentive absorbent core 4, having a substantially elongate shape, and being provided with upstanding guards 6 provided on the longitudinal left and right opposing side portions of the diaper.

When the upstanding guard 6 is sectioned into a free end region 65, a central region 66 and a basal end region 67 so as to trisect it in the widthwise direction, each region is provided with one upstanding guard elastic member 64, and the stress of the free end region 65 is larger than that of the other regions.

In particular, the disposable diaper 1 of this embodiment is provided with a plurality of upstanding guard elastic members 64 (64a', 64b', 64c') so that a gather is formed in the upstanding guard 6 over the entire region in the widthwise direction thereof, and the intervals t1' and t2' defined between the upstanding guard elastic members 64a' and 64b' and between 64'b and 64c', respectively, are almost equal.

The central region 66 has smaller stress than that of the free end region 65 and that of the basal end region 67. That is, in this embodiment, the stress of the free end region 65 is the largest, that of the basal end region 67 is the second largest, and that of the central region 66 is the smallest of all.

In particular, the free end region 65, the central region 66 and the basal end region 67 are provided with upstanding guard elastic members 64c', 64b' and 64a', respectively. The interval t1' between the upstanding guard elastic members 64a' and 64b' and the interval t2' between the upstanding guard elastic members 64b' and 64c' is almost the same.

The stress of the upstanding guard elastic member 64a' is preferably 5 to 90 cN, more preferably 5 to 70 cN, from the viewpoint of exhibiting highly fit properties and preventing the excessively strong touch to the skin by allowing the basal end region 67 to reliably receive outer forces by movements of the wearer.

The stress of the upstanding guard elastic member 64b' is preferably 5 to 80 cN, more preferably 5 to 60 cN, from the viewpoint of ensuring the stability of the free end region (fit region) during use by allowing the central region to function as a buffer region for buffering the deformation of the diaper body or forces caused by movements of the wearer.

The stress of the upstanding guard elastic member 64c' is preferably 10 to 100 cN, more preferably 10 to 80 cN, from the viewpoint of exhibiting good fit properties and preventing an excessively strong touch to the skin by reliably receiving forces from movements of the wearer.

The difference between the stress of the upstanding guard elastic member 64a' and upstanding guard elastic member 64b' or upstanding guard elastic member 64c' is preferably 5 cN or more, more preferably 10 cN or more, most preferably 10 to 50 cN, from the viewpoint of satisfactorily exhibiting the advantageous effect of each region, and from the view point of highly fit properties to the skin and good standing properties of the upstanding guard.

Since the elastic member is arranged to have different stresses, the stress of the free end region 65 is preferably 10 to 100 cN, more preferably 10 to 80 cN, from the viewpoint of exhibiting fit and antileakage properties at a high level, and softening the touch to the skin.

The stress of the central region 66 is preferably 5 to 80 cN, more preferably 5 to 60 cN, from the viewpoint of ensuring the stability of the free end region (fit region) during use by allowing the central region to function as a buffer region for buffering the deformation of the diaper body or forces caused by movements of the wearer.

The stress of the basal end region 67 is preferably 5 to 90 cN, more preferably 5 to 70 cN, from the viewpoint of exhibiting good fit properties and preventing an excessively strong touch to the skin by allowing the basal end region 67 to reliably receive forces from movements of the wearer.

The stress of the free end region 65 is preferably less than five times as large as the other regions, from the viewpoint of the coexistence of the pressure and fit to the skin. Specifically, the difference between the stress of the free end region 65 and that of the basal end region 67 or the central region 66 is preferably 15 cN or more in a 50% stretched condition, more preferably 10 cN or more, most preferably 10 to 50 cN, from the viewpoint of satisfactorily exhibiting the advantageous effect of each region, and from the viewpoint of highly fit properties to the skin and good standing properties of the upstanding guard.

The disposable diaper of this embodiment can be used in the same manner as the one of the first embodiment, exhibiting the same advantages, and can be produced in the same manner.

The disposable diaper of this embodiment can be made of any component members, which are conventionally used in the art of disposable diapers, without any particular limitation.

Various selections are available for the materials of the upstanding guard used in the first embodiment and the second embodiment. Liquid impermeable materials are preferred for the material of the upstanding guard from the viewpoint of exhibiting further improved antileakage properties. Among these, the embodiment using, as the material of the upstanding guard, a laminate sheet prepared by laminating a nonwoven fabric and a liquid impermeable film is the particularly preferable embodiment. There may be cases where the skin irritates from the use of the laminate sheet. In order to prevent this, it is effective to lower the film rigidity; for example, a film having a basis weight of less than 20 g/m$^2$ may be used. The preferred film is a nonporous moisture permeable sheet comprising an elastomer of a polyurethane and/or ester and a polyolefinic thermoplastic resin, which is disclosed in col. 3, line 1 to col. 4, line 27 of Japanese Patent Laid-open No. 9-201909. The nonwoven fabric and the liquid impermeable film can be laminated by a method of adhering using a hot melt adhesive, heat sealing, or ultrasonic sealing, which are conventionally used in the art of disposable diapers, without any particular limitation. In addition, as a liquid impermeable material, a film sheet made of thermoplastic resin may be used. A liquid impermeable and moisture permeable sheet prepared by mixing a filler with a thermoplastic resin and stretching the film made of the mixture may also be used. Examples of the thermoplastic resin include polyolefins such as polyethylene and polypropylene, polyesters and polyvinyl alcohol.

It is apparent that the absorbent article of the present invention is not limited to the aforementioned embodiments and that the present invention is changeable in various manner within the scope of the invention.

For example, the present invention is applicable to a sanitary napkin, a pad for incontinence or the like, other than a disposable diaper.

In the first embodiment, the form, material or the stretching percentage of the elastic member may be changed to thereby modify the stress of each elastic member.

The interval between the adjacent elastic members and the stress of each elastic member are not limited to the aforementioned range but are changeable, for example, as follows:

1: The interval arranged between the adjacent elastic members can be narrowed to make the stress of the region large, or the interval can be widen to make the stress of the region small, 2: The stress of the elastic member can be made large to make the stress of the region large, or the stress of each elastic member can be made small to make the stress of the region large.

The present invention is not intended to define the configuration of the upstanding guard but to define the stress of the region formed in the upstanding guard. Therefore, the configuration of the upstanding guard is changeable within the scope of the present invention.

In addition, another upstanding guard may be further applied to the waist portion. In addition, elastic members are applied to leg portions to thereby form a gather around the leg portions.

The third embodiment of an absorbent article according to the present invention will be described hereinafter.

Particularly, the points different from the first embodiment will be explained in detail hereinafter. Omission of explanation means that the points are the same as the first embodiment.

Figure 4:
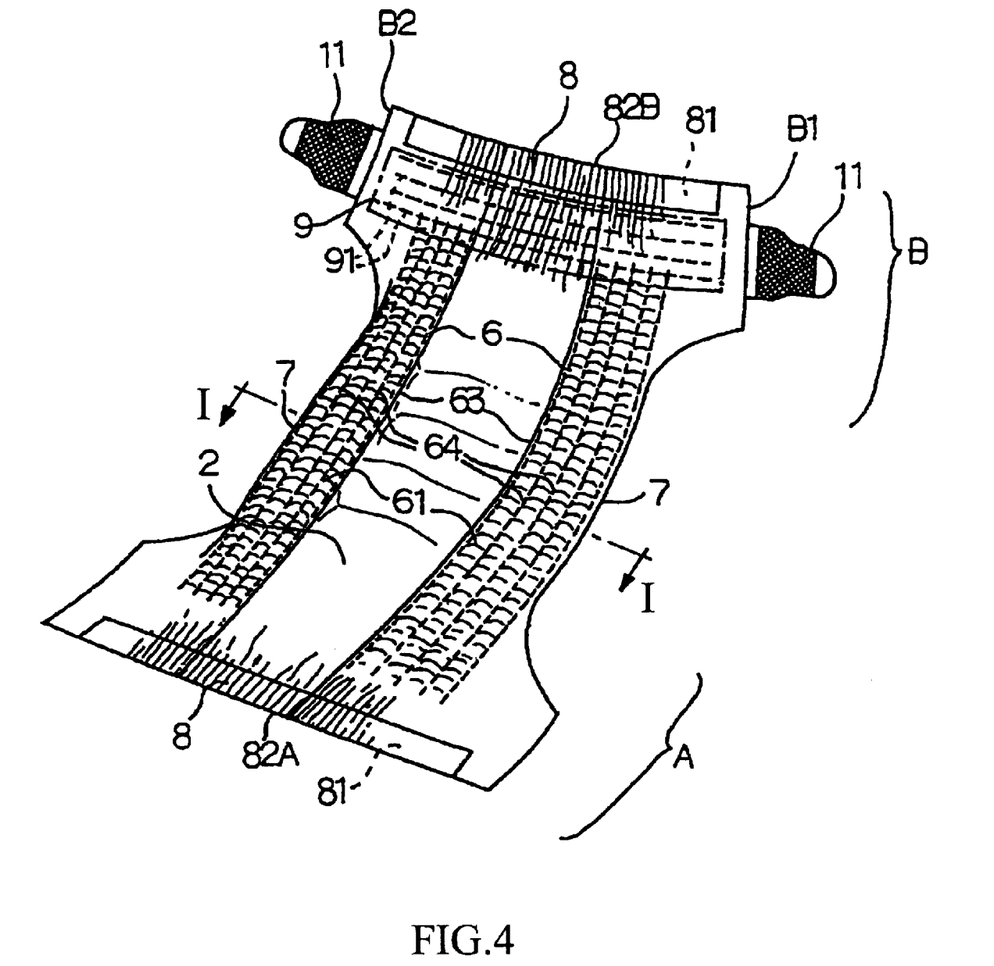
FIG. 4 is a perspective view showing the topsheet side of a disposable diaper according to a third embodiment of the present invention which is in a free (or relaxed) condition.
Figure 5:
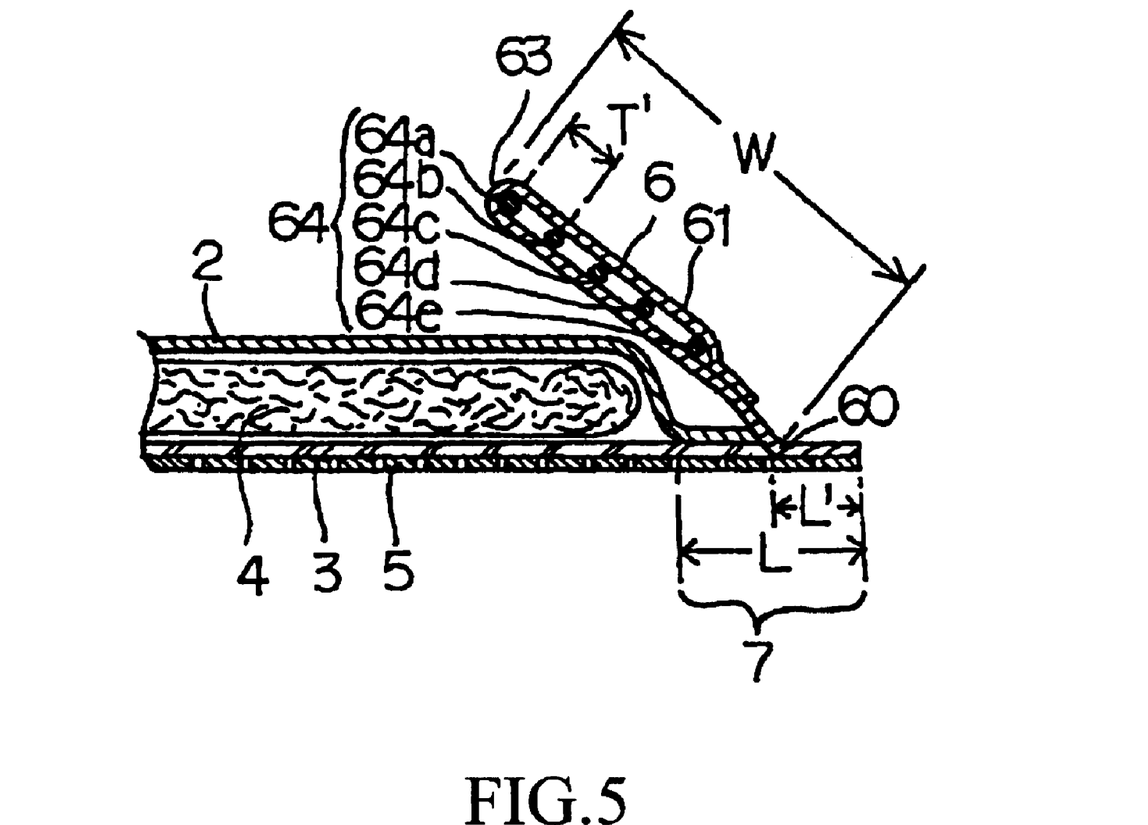
FIG. 5 is a sectional view taken along line I—I of FIG. 4 in which elastic members are in a stretched condition.

A disposable diaper 1 as an absorbent article of this embodiment includes, as shown in FIGS. 4 and 5, a liquid-permeable topsheet 2, a liquid-impermeable antileakage sheet 3 and a liquid-retentive absorbent core 4, a pair of leg portions 7 being formed outwardly of left and right opposing side edges of the absorbent core 4, a pair of upstanding guards 6 each having an upstanding guard elastic member(s) 64 (64a–64e) being formed on longitudinal left and right opposing side portions. By doing this, gathers are formed on each upstanding guard 6.

In the disposable diaper 1 of this embodiment, the absorbent core 4 is fixedly held in a sandwiching manner by and between both the topsheet 2 and the antileakage sheet 3. The topsheet 2 and the antileakage sheet 3 extend beyond the longitudinal left and right opposing side edges of the absorbent core 4, thereby forming a pair of left and right leg portions 7 which contact the legs of the wearer when in use on the wearer.

A pair of waist opening portions 8, one in a stomach-side portion A which is located on the stomach side of the wearer and the other in a back-side portion B which is located on the back side of the wearer when in use on the wearer, are each provided with a waist portion elastic member 81 on which waist gathers are formed. Each of opposing left and right side edge portions B1, B2 of the back-side portion B is provided with a tape fastener 11 for fastening the disposable diaper 1.

Each upstanding guard 6 is formed by disposing a strip-like sheet material 61 from a stomach-side waist opening edge 82A to a back-side waist opening edge 82B. Each sheet material 61 is firmly secured at its longitudinal end edge to the topsheet 2 on the waist opening portion 8 side and fixedly bonded at its longitudinal side portion to the topsheet 2 in the corresponding leg portion 7. Accordingly, a basal end 60 of the upstanding guard 6 is located on the topsheet 2 in the leg portion 7.

Disposed in the back-side portion B which is located on the back side of the wearer when in use on the wearer, is a back-side expansible portion 9. The back-side expansible portion 9 is formed by arranging a plurality of back-side elastic members 91 along a widthwise direction of the disposable diaper 1.

In the disposable diaper 1 according to this embodiment, the upstanding guards 6 are composed of the breathable sheet material 61, while the leg portions 7 are composed of the sheet material 61 and a breathable outer layer nonwoven fabric 5 which is disposed on an outer surface of the antileakage sheet 3. A plurality of the upstanding guard elastic members 64 are disposed between the basal end 60 and a free edge end 63 of each upstanding guard 6. The upstanding guard elastic member 64 is also disposed at the free edge end 63.

More specifically, a single upstanding guard elastic member 64 is disposed at the free edge end 63 and four upstanding guard elastic members 64 are disposed between the free end edge 63 and the basal end 60. The expression "a plurality of" as used above refers to a plurality of upstanding guard elastic members 64 being disposed at each upstanding guard 6 and does not refer to a plurality of upstanding guard elastic members 64 being necessarily disposed at the free edge end. The upstanding guard elastic members 64 are fixedly held in a sandwiching manner by and between those portions of the sheet material 61 folded back at the free edge end 63 through an adhesive agent. The upstanding guard elastic members 64 each are arranged in parallel to the free edge ends 63 and along the longitudinal direction of the disposable diaper 1.

The upstanding guard 6 is provided with an elastic member by arranging the interval between the adjacent elastic members as in the first embodiment or by making the interval equal and the stress of each elastic member different as in the second embodiment, whereby, when each guard is sectioned into a free end region, a central region and a basal end region so as to trisect it in the widthwise direction, the stress of the free end region becomes larger than that of the other regions.

The upstanding guards 6 are preferably from 10 to 150 mm in widthwise length W dimension.

Also, the number of the upstanding guard elastic members 64 are preferably from 3 to 20 pc. As shown in FIG. 5, an interval T' between adjacent upstanding guard elastic members 64 is preferably from 2 to 50 mm.

In the present invention, it is also accepted that the interval between the upstanding guard elastic member located at the free end 63 and the upstanding guard elastic member located proximate thereto is from 1 to 10 mm, and the intervals between the remaining adjacent upstanding guard elastic members are gradually increased by from 1 to 10 mm. Otherwise, the interval between the upstanding guard elastic member located at the free edge end 63 and the upstanding guard elastic member 64 located proximate thereto is from 4 to 40 mm, and the intervals between the remaining adjacent upstanding guard elastic members are gradually reduced by from 1 to 10 mm.

Also, in this embodiment, stress of the free edge end 63 are greater than that of those areas where all the remaining upstanding guard elastic members 64 are disposed. In addition, stress of the upstanding guard elastic member 64 disposed at free edge end 63 is preferably greater than that of all the remaining upstanding guard elastic members 64 disposed at the area between the free edge end 63 and the basal end 60.

Specifically, the stress of the upstanding guard elastic member 64 disposed at the free edge end 63 is preferably from 10 to 1000 gf and preferably greater by from 5 to 500 gf than that of all the remaining upstanding guard elastic members 64.

The "stress" can be measured in the following manner.
<Method for Measuring Stress of Elastic Members>

An elastic member was cut out having a length dimension of 150 mm, the same was subjected to a tensile test under the conditions of 100 mm in chuck distance and 300 mm/min in rate of pulling using a Tensilon tensile test machine (manufactured by Orientic Corp.) and the stress at 100% of stretching was measured.

The basal ends 60 are preferably located adjacent to the corresponding side edges of the antileakage sheet 3, respectively. In this embodiment, the basal ends 60 are located adjacent to the corresponding side edges of both the topsheet 2 and the antileakage sheet 3, respectively. That portion of the disposable diaper 1 which is located widthwise outwardly of each basal end 60 is composed only of a laminated sheet which is obtained by adhering the sheet material 61 and the outer layer nonwoven fabric 5 together.

The leg portions 7 are preferably from 5 to 50 mm in widthwise length L dimension (the length between the widthwise side edge of the diaper and the side edge of the absorbent core) and that portion which is composed only of the laminated sheet is preferably from 5 to 50 mm in widthwise length L' dimension. The basal ends 60 are formed by firmly securing the sheet material 61 to the outer layer nonwoven fabric 5 in the leg portions 7 through an adhesive agent.

The material for forming the component members of the disposable diaper 1 of this embodiment will be described next.

As the material for forming the topsheet 2, the antileakage sheet 3, the absorbent core 4, the waist portion elastic members 81 and the fastening tapes 11, there can be used without any particular limitation those which are normally used for conventional disposable diapers.

Both the sheet material 61 and the outer layer nonwoven fabric 5 are breathable (air-ventilating). They are preferably 500 sec/100 cc or less and more preferably 100 sec/100 cc or less in degree of air-permeability. By making the degree of air-permeability 500 sec/100 cc or less, the effective prevention of getting stuffy can be obtained.

Both the sheet material 61 and the outer layer nonwoven fabric 5 are preferably 3.0 $g/cm^2$ or more, and more preferably 5.0 $g/cm^2$ or more in water pressure resistance (water repellency). By making the water pressure resistance 3.0 $g/cm^2$ or more, it can be prevented that exudates seep out and leak from the upstanding guards or the exudates, which have climbed over the upstanding guards, seep and leak through the breathable portions in the leg portions.

Both the sheet material 61 and the outer layer nonwoven fabric 5 are preferably 1000 cN/50 mm or more and more preferably 1200 cN/50 mm or more in strength in the cross machine direction (CD). By making the strength 1000 cN/50 mm or more, it can be prevented that the fastening tapes are peeled off at their root portions.

The material for forming the sheet material for satisfying such conditions may include a spunbond nonwoven fabric, a spunbond/meltblown/spunbond nonwoven fabric (SMS), a spunbond/meltblown/meltblown/spunbond nonwoven fabric (SMMS), a heatroll nonwoven fabric, an airthrough nonwoven fabric and the like. Similarly, the material for forming the outer layer nonwoven fabric may include a spunbond nonwoven fabric, SMS, SMMS, a heatroll nonwoven fabric, an airthrough nonwoven fabric and the like.

The degree of air-permeability, the water pressure resistance and the strength can be measured in the following manner.

Degree of Air-Permeability: Measured in accordance with JIS-P8117. That is, a sheet was cut having the dimensions of 70×70 mm and the time required for air of 100 ml to pass therethrough was measured using an air-permeability degree measuring instrument (Oken type air-permeability degree measuring instrument).

<Water Pressure Resistance>

Figure 9:
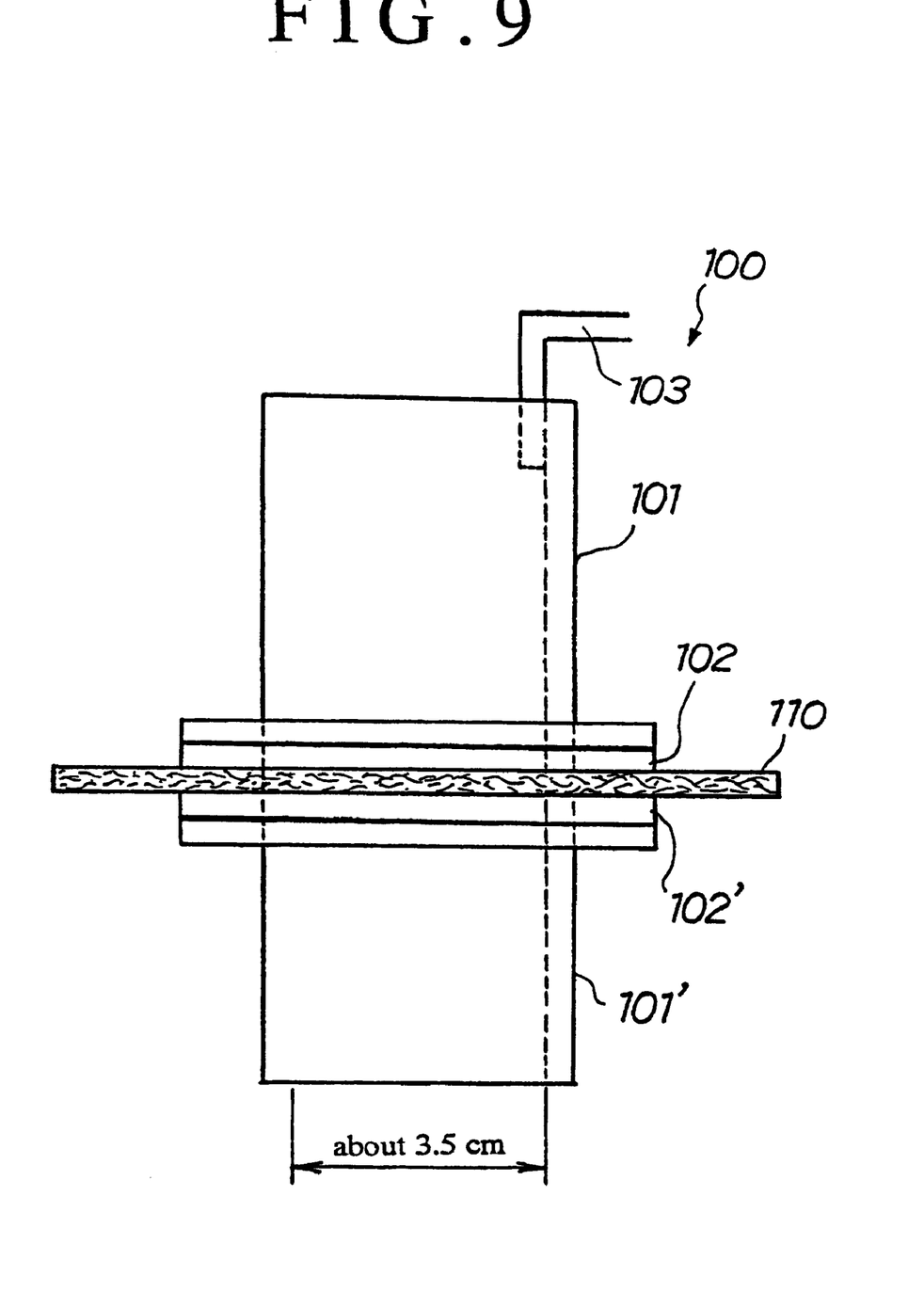
FIG. 9 is a schematic view showing the apparatus used for the water-proof test.

Water pressure resistance is measured with the use of an apparatus 100, as shown in FIG. 9, wherein two cylindrical tubes 101, 101' having an inner diameter of about 3.5 cm and a sectional area of 9.6 cm$^2$ sandwich a test sheet (nonwoven fabric or sheet material) 110 through rubber packings 102, 102', the cylindrical tubes 101, 101', rubber packings 102, 102', and the test sheet 110 are fixed with a clamp (not shown in Figures), and the upper cylindrical tube 101 is provided with a tube 103 on the upper end thereof. Through the tube 103, physiological saline is poured into the cylindrical tube 101 at a rate of 4 g a minute, and the time period until the physiological saline leaks to the lower cylindrical tube 101' passing through the test sheet 110 is measured. The data of the time thus obtained are applied to the measurement formula mentioned below to determine water pressure resistance.

Water pressure resistance (g/cm$^2$)=measuring time (seconds)×(4 g/60 seconds)/9.6 cm$^2$ The physiological saline was prepared by solving it in ion exchange water to give a content of 10.9% by weight.

Strength: A test piece was cut out having a width of 25 mm in a machine direction (MD) and a length of 150 mm in a direction perpendicular to the MD (ie., cross machine direction (CD)). This test piece was subjected to a tensile test under the conditions of 50 mm in chuck distance and 300 mm/min in rate of pulling in the cross machine direction (CD) using a Tensilon tensile test machine (manufactured by Orientic Corp.), and the strength of the test piece, when fractured, was measured.

As the upstanding guard elastic member 64, there can be used elastic members known in the art without any limitation, as long as they satisfy the above stress. The upstanding guard elastic member(s) disposed at each free edge end and the remaining upstanding guard elastic members may be formed of different materials so that their stress will be different. Otherwise, they may be formed of the same material but with differences in stretch percentage, etc.

The disposable diaper 1 of this embodiment can be used in the same manner as the typical flat type disposable diaper.

In the disposable diaper 1 of this embodiment, since a plurality of the upstanding guard elastic members 64 are disposed at each upstanding guard 6, pocket portions are formed each between adjacent upstanding guard elastic members 64. Accordingly, the waste materials, which should have climbed over the upstanding guards 6, would be caught by those pocket portions, thus enabling to effectively prevent the leakage from the leg portions. Moreover, since the leg portions 7 are composed only of a breathable sheet, the disposable diaper 1 exhibits a good breathability and does not get stuffy in use on the wearer.

The "pocket portions" as used herein include not only those which are continuously formed in the longitudinal direction of the disposable diaper but also those consisting of a plurality of concavities which are intermittently formed. Especially, in the case where the gathers are formed by properly arranging the upstanding guard elastic members as in this embodiment, a plurality of concavities and convexities are formed between adjacent upstanding guard elastic members as the gathers are formed. The "pocket portions" as used in this specification include those consisting of a plurality of concavities which are intermittently formed in the longitudinal direction of the disposable diaper between the adjacent upstanding guard elastic members.

The disposable diaper of this embodiment can be obtained by fixedly holding a sandwich of the absorbent core and the waist elastic members between both the topsheet and the antileakage sheet. Then, the sheet material, on which the plurality of elastic members are arranged at predetermined intervals, is bonded at a predetermined position in accordance with the method.

Although the disposable diaper 1 having no gathers in the leg portions 7 is exemplified in the third embodiment, the present invention should not be limited to this. Instead, the disposable diaper may have leg gathers formed by properly arranging the elastic members in the leg portions. By doing so, the effect of leakage prevention can be enhanced owing to the function of the leg gathers.

Although a flat type disposable diaper is exemplified in the third embodiment, the present invention is also applicable to a briefs type disposable diaper (in which the longitudinal direction is the up and down directions of the disposable diaper), a sanitary napkin and the like.

Although the disposable diaper in which the basal end 60 of each upstanding guard is located in the leg portion 7, i.e., the basal end 60 is not located on the absorbent core, is exemplified, the present invention is not limited to this. The basal end 60 may be located on the absorbent core 4. By doing so, even if the waste materials should climb over the upstanding guards, they would be absorbed by the absorptive portions which are located outwardly of the basal ends. Accordingly, the effect of leakage prevention is more enhanced.

Further, a waist portion upstanding guard having an upstanding guard elastic member(s) may be formed both on the stomach side portion and the back-side portion (or, alternatively, on one of the portions) in order to prevent leakage from the waist portion.

It is also accepted that the upstanding guard or the elastic member(s) disposed at the upstanding guard is curved such that an end portion of the upstanding guard or the elastic member(s) disposed at the upstanding guard is located adjacent to a support portion of a tape fastener.

Further, that area of the upstanding guard between the basal end portion and the free end portion may be laminated with either a liquid-permeable or a liquid-impermeable film.

The upstanding guard itself may be composed of an expandable sheet material.

Further, the stress of the upstanding guard elastic member (s) disposed at the free edge end may be made greater than that of the remaining elastic members by bundling a plurality of elastic members on the free edge end or by other means.

As the material constituting the absorbent core, there can be used a water-repellent mount, a nonwoven fabric and a liquid-impermeable film. Also, a lower portion and side portions of the absorptive portion may be covered with those materials. By doing so, it can effectively be prevented that the waste materials, which have been once absorbed, are caused to seep out of the absorbent core by the wearer's body pressure.

The fourth embodiment of an absorbent article according to the present invention will be described hereinafter.

Particularly, the points different from the first embodiment will be explained in detail hereinafter. Where detailed explanations are omitted, the explanation of the first embodiment should be pertinently applied thereto.

Figure 6:
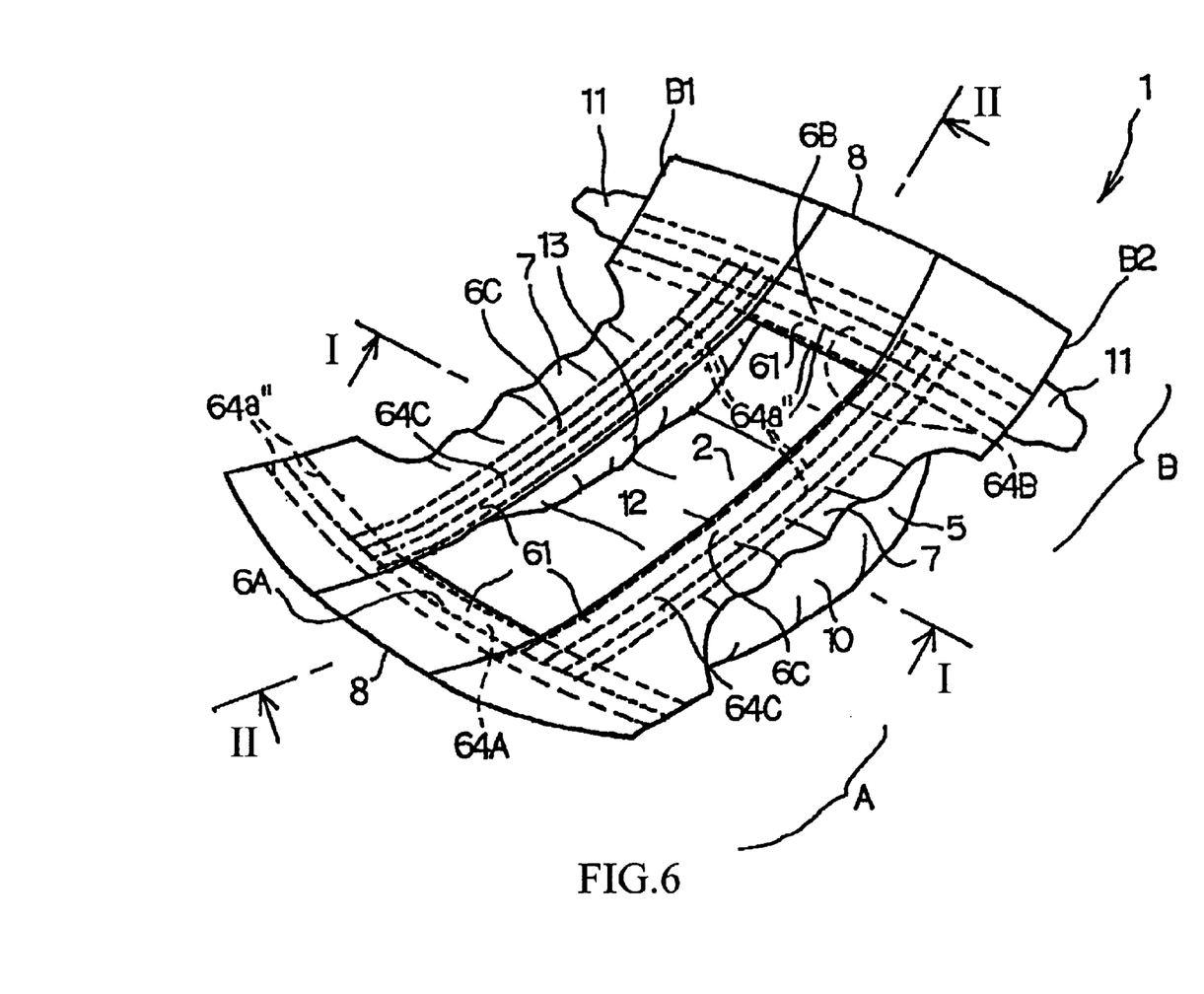
FIG. 6 is a perspective view of a disposable diaper according to a fourth embodiment of the present invention viewed from the topsheet side of a disposable diaper in a free (or relaxed) condition.
Figure 7:
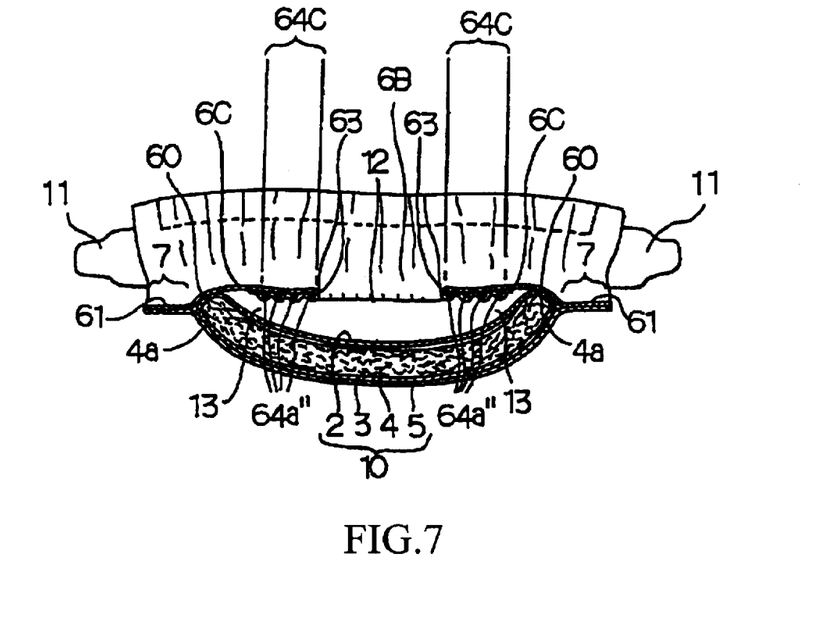
FIG. 7 is a sectional view taken along line III—III of FIG. 6.
Figure 8:
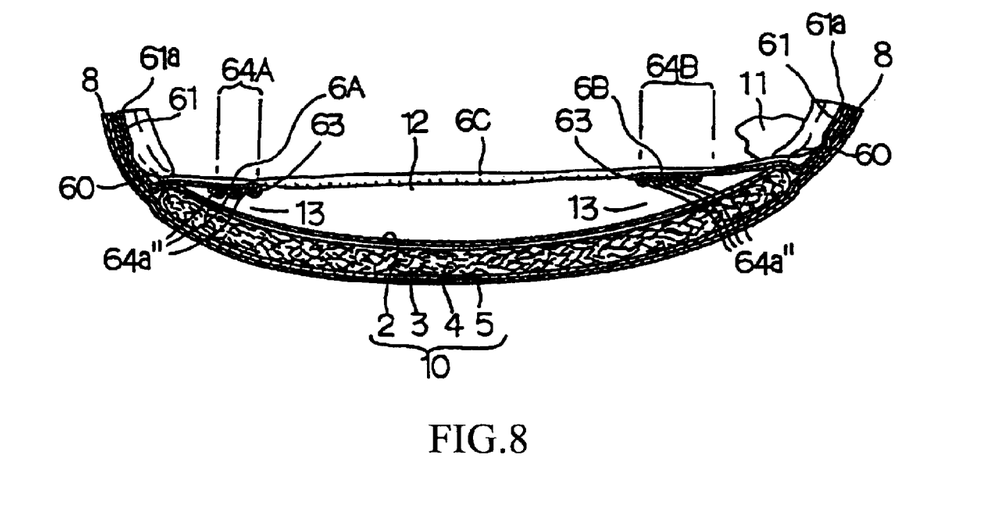
FIG. 8 is a sectional view taken along line II—II of FIG. 6.

A disposable diaper 1 as an absorbent article of this embodiment has, as shown in FIGS. 6, 7 and 8, a substantially elongate absorptive body 10 including a liquid-permeable topsheet 2, a liquid-impermeable antileakage sheet 3 and a liquid-retentive absorbent core 4.

The surface of the antileakage sheet 3 is provided with an outer layer nonwoven fabric 5. The outer layer nonwoven fabric 5 extends such that the both side edges thereof locate outwardly of the side edges 4a of the absorbent core 4. The extended portion of nonwoven fabric 5 forms a pair of left and right leg portions 7.

Therefore, the disposable diaper 1 of this embodiment is provided with upstanding guards on the longitudinal left and right opposing side edges and the longitudinal opposing end edges of the absorptive body 10, respectively. Each upstanding guard is provided with a wide elastic portion. That is, the upstanding guard having wide contracting portion as the back-side expandable portion is arranged on the back-side portion.

The disposable diaper 1 of this embodiment includes, as upstanding guards 6, side upstanding guards 6C, 6C arranged on the left and right opposing sides of the diaper, back-side upstanding guard 6B arranged on the back-side portion B and stomach-side upstanding guard 6A arranged on the stomach-side portion A. In addition, the elastic portion includes a side elastic portion 64C arranged on the side upstanding guards 6C, 6C, a back-side elastic portion 64B arranged on the back-side upstanding guard 6B and a stomach-side elastic portion 64A arranged on the stomach-side upstanding guard 6A.

In more detail, the side upstanding guards 6C, 6C, are formed on left and right opposing sides of the diaper by disposing sheet materials 61 for forming an upstanding guard. The sheet materials 61 are extended beyond the respective opposing sides of the absorbent core 4 and sealed to the outer layer nonwoven fabric 5.

The back-side upstanding guard 6B and stomach-side upstanding guard 6A are formed on the back-side portion B and stomach-side portion A, respectively, by disposing the sheet materials 61 in such a manner that the outer end edge 61a thereof locates at the end edge of the waist opening portion 8.

The upstanding guards 6A, 6B, 6C and 6C each fixedly adhere to the topsheet 2 in the upper position of the absorbent core 4 to thereby form a basal end 60.

The side elastic portions 64C, 64C, back-side elastic portion 64B and stomach-side elastic portion 64A are formed by arranging a plurality of string-like elastic members 64a" at a predetermined interval. Each elastic member 64a" is provided along the longitudinal direction and over the generally entire area through the longitudinal direction of the upstanding guard.

In connection with the width of each upstanding guard, i.e., the length from the free edge end 63 to the basal end 60, it is preferable that the width of the side upstanding guards 6C, 6C is 20 to 100 mm, that of the back-side upstanding guard 6B is 20 to 100 mm and that of the stomach-side upstanding guard 6A is 20 to 80 mm.

The width of the elastic portions 64A, 64B and 64C are each preferably 10 mm or more. The width of 10 mm or more enables to enhance the fit property for contacting the skin on surface and to fully exhibit the desired advantages of the present invention.

The side elastic portions 64C, 64C are each formed by disposing four pieces of elastic members 64a; the back-side elastic portion 64B is formed by disposing four pieces of elastic members 64a; and the stomach-side elastic portion 64A is formed by disposing three pieces of elastic members 64a;

Thus, "the wide elastic portion" refers to the area where the contracting property exhibits by the arrangement of elastic members or the like. For example, the area of the side elastic portion 64C is from the elastic member closest to the free edge 63 to the one closest to the basal end.

The side upstanding guard 6C, back-side upstanding guard 6B and stomach-side upstanding guard 6A each are provided with an elastic member by arranging the interval between the adjacent elastic members as in the first embodiment or by making the interval equal and the stress of each elastic member different as in the second embodiment, whereby, when each guard is sectioned into a free end region, a central region and a basal end region so as to trisect it in the widthwise direction, the stress of the free end region becomes larger than that of the other regions.

The side upstanding guard 6C, the back-side upstanding guard 6B and the stomach-side upstanding guard 6A are mutually connected.

That is, in this embodiment, the side upstanding guards 6C, the back side upstanding guard 6B and the stomach side upstanding guard 6A are in a form of belt, and the longitudinal end portions of the side upstanding guards 6C are joined to the longitudinal end portions of the back-side upstanding guard 6B and the stomach side upstanding guard 6A, respectively, whereby a rectangular opening portion 12 is formed by each upstanding guard.

The upstanding guards 6A, 6B, 6C, 6C are, as shown in FIGS. 7 and 8, a plate-like upstanding guard forming almost horizontal surface. The upstanding guards 6A, 6B, 6C, 6C of plate-like form are brought into direct surface contact with the wearer's skin in use.

The upstanding guards 6A, 6B, 6C, 6C are connected such that the elastic members 64a" provided thereon are overlaid with each other, i.e., such that the longitudinal end portions of the elastic member 64a" in the side elastic portions 64C, 64C are located on the stomach-side elastic portion 64A and back-side elastic portion. 64B, respectively. By the contracting force of the elastic portions 64A, 64B, 64C, 64C, the absorptive body of the disposable diaper comprising the absorbent core, topsheet, and antileakage sheet is curved so as to give a generally cup form. Further, the upstanding guards 6A, 6B, 6C, 6C and in the lower position thereof between the upstanding guards 6A, 6B, 6C, 6C and the topsheet 2.

The size of the opening portion 12 can be selected depending on the diaper for infants or the diaper for adults.

In the disposable diaper 1 of this embodiment, an elastic member is not disposed in the leg portion 7.

The disposable diaper 1 of this embodiment can be used in the same manner as the typical flat type disposable diaper.

Since the disposable diaper 1 of this embodiment is structured as mentioned above, the upstanding guards 6A, 6B, 6C, 6C each contact the wearer's skin in the surface, whereby the fit property by the upstanding guards cannot be prevented in any wearing condition and good fit property is exhibited. In addition, the discharging portion of the wearer is located at the opening portion 12 with a pocket portion 13 being formed around the surrounding area, so that the waste materials are allowed to be discharged directly towards the absorbent core and the waste materials, which cannot be absorbed at a time and migrated over the topsheet, can be stocked in the pocket portion 13 for a time being to be reabsorbed. Thus, the disposable diaper 1 of this embodiment is excellent in the antileakage property.

Now, a method of producing the disposable diaper of this embodiment will be described.

The method of the producing the disposable diaper of this embodiment comprises steps of:

transferring continuous bodies each of first and second sheet materials for forming the upstanding guards provided on the left and right opposition sides in parallel with each other, applying a continuous body of a third sheet material for forming the front- and back-side upstanding guards to the continuous bodies of the first and second sheet materials so as to cross thereto, thereby forming a continuous body of composite sheet material in a ladder shape in which the first, second and third sheet materials for forming upstanding guards are combined, interposing an absorbent core between a continuous body of an antileakage sheet and a continuous body of a topsheet, thereby forming a continuous body of an absorptive body, disposing the continuous body of composite sheet material at a predetermined position of the continuous body of the absorptive body thus obtained, and finally cutting the resultant continuous body at a predetermined position to thereby obtain an individual absorbent article.

The description of the fourth embodiment exemplifies the upstanding guards in which the basal end 60 thereof is located on the absorbent core 4, but the present invention should not be limited to this. The basal end 60 may be located on the leg portion 7.

In addition, the present invention should not be limited to the exemplified disposal diaper which has no gathers in the leg portion but may be provided with leg gathers.

The second embodiment is explained by exemplifying a flat type disposable diaper, but the present invention, which should not be limited to this, is applicable to a shorts type disposable diaper comprising the fixture sealing of the left and right opposing sides of the absorptive body, as well as an incontinent pad or a sanitary napkin.

The fourth embodiment exemplifies the diaper having upstanding guards on the both of the front side and rear side of the disposable diaper, i.e., both on the stomach-side portion and the back-side portion of the diaper, but the upstanding guard may be disposed at least on either one side thereof.

In addition, the absorbent core may be divided in a longitudinal direction and/or in the width direction, or provided with some cuts. Specifically, the absorbent core may be formed by arranging three pieces of strip rectangular absorbent cores in line, provided with cuts on the both lateral sides or both end portions of the diaper, whereby the formation of the opening portion 12 is stably maintained and slippage is prevented.

The exemplified elastic portion 64 is formed by a plurality of string elastic members, but elastic members in a form of belt can be used. Alternatively, the elastic portion may be formed by the sheet material having elastic contractivity.

Industrial Applicability

The absorbent article of the present invention has the upstanding guards giving nice and comfortable fit to the wearer's skin and exhibits excellent anitleakage properties.

This application claims the priority of Japanese Patent Application Nos. 11-63345 filed Mar. 10, 1999 and 11-348995 filed Dec. 8, 1999, which are incorporated herein by reference.

What is claimed is:

1. An absorbent article which comprises a liquid-permeable topsheet, a liquid-impermeable antileakage sheet and a liquid-retentive absorbent core, said absorbent article being provided with upstanding guards along longitudinal left and right opposing side portions thereof, wherein each of the upstanding guards are provided with a plurality of upstanding guard elastic members which form a gather in a widthwise direction of each upstanding guard; and wherein each upstanding guard is sectioned in the widthwise direction into a free end region, a central region and a basal end region, a stress in the free end region being larger than that of the other regions, and the central region has a smaller stress than that of the free end region and the basal region, and the stress of the free end region is from 10 cN to 100 cN.

2. The absorbent article according to claim 1, wherein the plurality of upstanding guard elastic members are arranged such that the intervals therebetween are unequal in the widthwise direction of each upstanding guard.

3. The absorbent article according to claim 1, wherein the plurality of upstanding guard elastic members have a non-uniform stress.

4. The absorbent article according to claim 1, wherein the plurality of upstanding guard elastic members are arranged such that the intervals therebetween are equal in the widthwise direction of each upstanding guard, and the stress of each upstanding guard elastic members is non-uniform.

5. The absorbent article according to claim 1, wherein each upstanding guard comprises a breathable sheet material, wherein a pair of leg portions of the absorbent article comprise the respective sheet materials and a breathable outer layer nonwoven fabric disposed on a surface of the antileakage sheet.

6. The absorbent article according to claim 5, wherein the sheet material and the outer layer nonwoven fabric are 1000 cN/50 mm or more in cross machine direction strength.

7. The absorbent article according to claim 1, wherein basal end regions of the upstanding guards adjoin respective side edges of the antileakage sheet.

8. The absorbent article according to claim 1, wherein upstanding guards are also formed on a stomach-side portion and a back-side portion, and wherein the upstanding guards formed on the left and right opposing side portions of the absorbent article and the upstanding guards formed on the stomach-side portion and the back-side portion are mutually connected.

9. The absorbent article according to claim 1, wherein each region is provided with one upstanding guard elastic member.

10. The absorbent article according to claim 1, wherein the free end region is provided with two upstanding guard elastic members and each of the central region and basal region is provided with one upstanding guard elastic member.

11. The absorbent article according to claim 10, wherein each upstanding guard is sectioned in the widthwise direction into a free end region a central region and a basal end region the stress in the free end region being larger than that of the other regions and $$t1+t2+t3 \leq T,$$

and $$t3 \leq T/3$$

wherein t1 is an interval between the one elastic member of the basal end region and the one elastic member of the central region, t2 is an interval between the one elastic member of the central region and the closest of the two elastic members of the free end region, t3 is an interval between the two elastic members of the free end region.

12. The absorbent article according to claim 1, wherein the absorbent article is a disposable diaper.

13. The absorbent article according to claim 1, wherein the absorbent article is a sanitary napkin.

14. The absorbent article according to claim 1, wherein the absorbent article is an incontinence pad.

15. The absorbent article according to claim 1, wherein pocket portions are formed between adjacent upstanding guard elastic members for preventing leakage therefrom.

16. The absorbent article according to claim 1, further comprising a pair of leg portions, wherein pocket portions are defined between said upstanding guards and, said topsheet; and wherein no gathers are formed in the leg portions.

17. The absorbent article according to claim 1, wherein the stress of the basal end region is from 5 cN to 90 cN.

18. The absorbent article according to claim 1, wherein the stress of the central region is from 5 cN to 80 cN.

19. The absorbent article according to claim 1, wherein a difference between the stress of the free end region and the basal end region or the central region at a 50% stretched condition is 5 cN or more.

* * * * *